US010989774B2

(12) United States Patent
Zhang (10) Patent No.: US 10,989,774 B2
(45) Date of Patent: Apr. 27, 2021

(54) RETRACTABLE MAGNETIC RESONANCE IMAGING (MRI) MAGNET FIELD ASSEMBLY FOR AN EQUINE MRI SYSTEM

(71) Applicant: SIGWA COMPANY, LLC, Acton, MA (US)

(72) Inventor: Fengling Zhang, Acton, MA (US)

(73) Assignee: Sigwa Company, LLC, Acton, MA (US)

( * ) Notice: Subject to any disclaimer, the term of this patent is extended or adjusted under 35 U.S.C. 154(b) by 0 days.

(21) Appl. No.: 16/553,899

(22) Filed: Aug. 28, 2019

(65) Prior Publication Data

US 2021/0063515 A1    Mar. 4, 2021

(51) Int. Cl.
*G01R 33/38*     (2006.01)
*A61B 5/055*     (2006.01)
*G01R 33/3815*   (2006.01)

(52) U.S. Cl.
CPC .......... *G01R 33/3802* (2013.01); *A61B 5/055* (2013.01); *G01R 33/3815* (2013.01); *A61B 2503/40* (2013.01)

(58) Field of Classification Search
CPC  A61B 5/055; A61B 2503/40; G01R 33/3802; G01R 33/3815
See application file for complete search history.

(56) References Cited

U.S. PATENT DOCUMENTS

| 6,567,683 | B1 * | 5/2003 | Knuettel ............. A61B 5/0555 600/410 |
| 6,845,262 | B2 | 1/2005 | Albert et al. |
| 8,616,767 | B2 * | 12/2013 | Kenny ................ A61B 6/4208 378/208 |
| 9,508,256 | B2 | 11/2016 | Brady-Kalnay et al. |
| 9,555,135 | B2 | 1/2017 | Frank et al. |
| 2005/0088178 | A1 * | 4/2005 | Bolas ................. G01R 33/3806 324/318 |
| 2010/0102811 | A1 | 4/2010 | Demas et al. |
| 2014/0292328 | A1 | 10/2014 | Brady-Kalnay et al. |
| 2016/0082132 | A1 | 3/2016 | Yang et al. |

* cited by examiner

*Primary Examiner* — Gregory H Curran
(74) *Attorney, Agent, or Firm* — Kanika Radhakrishnan; Evergreen Valley Law Group (57) ABSTRACT

The present disclosure provides a vertically retractable magnet field assembly for a Magnetic Imaging Resonance (MRI) system. The assembly can move from an upward raised position to a downward retracted position, and vice versa. The assembly includes a magnet configured with a bore for imaging a body portion of a subject. The bore defines an inner surface of the magnet and extends along a longitudinal axis of the magnet. The magnet includes at least one flux generating element disposed within the magnet and oriented such that each of the at least one flux generating element surrounds the bore. Each of the at least one flux generating element is configured to generate a magnetic field for magnetizing the body portion positioned within the bore to generate a visual representation of an anatomy of the body portion.

22 Claims, 10 Drawing Sheets

RETRACTABLE MAGNETIC RESONANCE IMAGING (MRI) MAGNET FIELD ASSEMBLY FOR AN EQUINE MRI SYSTEM

TECHNICAL FIELD

The present disclosure relates generally to a Magnetic Resonance Imaging (MRI) magnet and gradient assembly (herein called a Magnet Field Assembly) and, more particularly to, a vertically retractable MRI Magnet Field Assembly for a MRI system, such as, but is not limited to, an equine MRI system.

BACKGROUND

In the medical field, imaging techniques, such as MRI techniques, are typically used for generating visual representations of an anatomy of a body of a subject (e.g., an animal, a human, etc.) for clinical analysis and medical intervention. The MRI technique generates detailed spatial images of the body, enabling accurate and precise medical diagnosis by a medical practitioner. The MRI technique is typically employed to the subject via MRI scanners or devices.

The MRI scanners generally include a large magnet with a cylindrical tunnel, also called a bore, in which the subject is positioned. The subject is required to remain still for a predetermined duration of time for scanning a body portion. Hence, these MRI scanners are typically employed for human subjects, due to the requirement of subject cooperation. As such, these MRI scanners are unsuitable for imaging subjects such as equines or other animals, since such subjects i.e. animals do not ordinarily cooperate during the MRI scanning. The medical practitioner may, therefore, administer anaesthesia to the animal, for ensuring cooperation during the procedure. Administering anaesthesia to animals may carry significant risk to the health of the animals. Moreover, the dimensions of the MRI scanner may not be sufficiently large for accommodating large animals such as horses and thus the MRI scanner may only be able to scan extremities of limbs of large animals. To imaging horse legs in the human MRI machine, horses needs to undergo general anaesthesia and lay on its side. A typical horse is too big to fit its body into the tunnel. MRI imaging requires the region of interest be positioned at the isocenter of the bore, which typically means 60-80 cm into the tunnel. To image horse hoof or legs, special positioning needs to be considered to have the region of interest as close to the isocenter as possible.

To achieve high image quality, the MRI magnets must be high field strength. The high field magnets are typically made as a cylindrical tube-like structure using superconducting materials. Higher field magnets result in better imaging performance. However, if the bore of the cylindrical magnet is surrounding the leg of a conscious standing animal, the animal is in danger of being injured should it move away suddenly with its leg trapped in the bore of the MRI machine. When imaging a conscious animal, such as a standing horse, one must be ready for the animal to move unpredictably. Particularly a standing horse may get startled and move suddenly.

The high field clinical MRI scanners generally include a large superconducting magnet, consisting of a plurality of flux generating elements made of superconducting wire. The plurality of flux generating elements are required to be maintained below a critical temperature via a suitable cooling system during operation. Traditionally, for maintaining cryogenic operating conditions, the flux generating elements are immersed in a liquid helium bath, whose temperature is maintained by the cooling system. As such, the flux generating elements generate the required magnetic field for magnetizing the body portion of the subject. However, the liquid helium used in the scanners is typically associated with major maintenance issues, such as but not limited to, helium blow-off. In such scenarios, the helium is required to be refilled, which adds to the maintenance of the MRI scanner which is worsened by the repetitive liquid helium global shortage. Additionally, the leaked helium could freeze human tissues instantly and thus, poses serious cold burn hazards. Moreover, the expansion ratio of the helium going from liquid form to gaseous form is about 1:757. As such, in the event of a sudden loss of superconductivity, the helium is subjected to cryogenic boiling and expansion leading to over pressurization of the scanner. The expansion may result in the explosion of the scanner, which is hazardous. Though suitable vent pipes or safety systems may be employed in the scanner for relieving the gaseous helium, such constructions may make the device expensive and cumbersome for maintenance. The superconducting magnets cooled by liquid helium are also called "wet" magnets. In comparison, cryogen-free superconducting magnets, also called "dry" magnets, do not use cryogens such as liquid helium. Compact magnets can be cryogen-free, so that no liquid helium or other liquid cryogens are needed, eliminating the maintenance cost, construction cost, and potential safety issues associated with liquid helium. The "dry" magnet offers the advantages of 1) safe and economical operation; 2) free rotation of magnetic field axes; 3) ease of handling; and 4) compact and light. There is a third in-between magnet option called the cryogen-less superconducting magnet which uses smaller amount of liquid-cryogen for superconducting magnet, compared with the "wet" magnet.

Therefore, there is a need for techniques which can overcome one or more limitations stated above in addition to providing other technical advantages.

SUMMARY

The present invention uses a compact, vertically retractable magnet and gradient assembly (Magnet Field Assembly) that allows imaging subjects, such as horses, to be awake and standing while the Magnet Field Assembly moves up from the floor to fit one leg (or other body part such as hoofs) in the bore for imaging the leg (or other body part such as hoofs) of interest and safely retracts into the floor should animal moves from the imaging position. The vertically retractable Magnet Field Assembly is designed to fit a standing animal comfortably and is mounted to a mechanism that safely retracts the Magnet Field Assembly into the floor if the animal walks to or away from the imaging position. Because the Magnet Field Assembly safely retracts, the MRI magnet can be made with a cylindrical bore. This allow the use of superconducting technology, which greatly improves the field strength of the MRI system and thereby the imaging performance. The compact magnet could be a "wet", "dry", or cryogen-less superconducting magnet. However, the "dry" superconducting magnet option is usually preferred because it eliminates the need for liquid helium, and thereby eliminates helium maintenance issues and eliminates the need for magnet quench vent pipes going all the way to the roof, which are required for "wet" magnet safety. For a retractable Magnet Filed Assembly, the absence of liquid helium and magnet quench pipes gives the "dry" superconducting magnet option the added benefit of freedom of rotation and movement, safer, elegant, and convenient for a retractable assembly from a product engineering, operation, and product reliability perspective.

Various embodiments of the present disclosure provide a vertically retractable Magnet Assembly for a Magnetic Imaging Resonance (MRI) system. The assembly includes a magnet and is configured to have a bore for receiving the targeted parts of a subject. The bore defines an inner surface of the magnet and extends along a longitudinal axis of the magnet. At least one flux generating element is disposed within the magnet and oriented such that each of the at least one flux generating element surrounds the bore. Each of the at least one flux generating element is configured to generate a magnetic field for imaging the body portion positioned within the bore to generate a visual representation of an anatomy of the body portion.

In an embodiment, the present disclosure provides the retractable magnet and gradient assembly (Magnet Field Assembly) for an MRI system. The assembly includes a Magnet Assembly and is configured to have the bore for receiving the targeted parts of the subject. The bore defines the inner surface of the magnet and extends along a longitudinal axis of the magnet. The at least one flux generating element is disposed within the magnet and oriented such that each of the at least one flux generating element surrounds the bore. Each of the at least one flux generating element is configured to generate the magnetic field for imaging the body portion positioned within the bore to generate a visual representation of an anatomy of the body portion. A gradient coil is mounted to the inner surface and extending along a length of the bore. The gradient coil is configured for spatial encoding of the magnetic field. A transmit coil may be mounted onto an exposed inner surface of the gradient coil and extending along a length of the gradient coil. The transmit coil is configured to transmit Radio Frequency (RF) pulse rotating net magnetization away from its alignment with the main magnetic field. In one configuration, it is optional to have a transmit coil as part of the retractable Magnet Field Assembly. An alternative is to not to mount a transmit coil on the retractable Magnet Field Assembly and instead have a transmit coil located local to receive coils. A magnet shielding element is mounted around the side surface of a bottom portion of the magnet. The magnet shielding element is configured to attenuate a fringe field generated by the magnet primary flux generating element. In one configuration, it is optional to have a magnet shielding element as part of the retractable Magnet Field Assembly.

In another embodiment, the present disclosure provides an equine MRI system. The system includes the retractable Magnet Field Assembly configured for imaging the region of interest of a horse. The assembly includes a magnet assembly and is configured to have the bore for receiving the body portion of a horse. The bore defines the inner surface of the magnet and extends along a longitudinal axis of the magnet. The at least one flux generating element is disposed within the magnet and oriented such that each of the at least one flux generating element surrounds the bore. Each of the at least one flux generating element is configured to generate the magnetic field for imaging the body portion positioned within the bore to generate a visual representation of an anatomy of the body portion. A gradient coil is mounted to the inner surface and extending along a length of the bore. The gradient coil is configured for spatial encoding of the magnetic field. A transmit coil may be mounted onto an exposed inner surface of the gradient coil and extending along a length of the gradient coil. The transmit coil is configured to transmit Radio Frequency (RF) pulse rotating net magnetization away from its alignment with the main magnetic field. In one configuration, it is optional to have a transmit coil as part of the retractable Magnet Field Assembly. An alternative is to not to mount a transmit coil on the retractable Magnet Field Assembly and instead have a transmit coil located local to receive coils. A magnet shielding element is mounted around the side surface of a bottom portion of the magnet. The magnet shielding element is configured to attenuate a fringe field generated by the primary flux generating element. In one configuration, it is optional to have a magnet shielding element as part of the retractable Magnet Field Assembly for the equine MRI system. A positioning system is coupled to the magnet and configured to adjust position of the magnet in at least a coordinate axes between a first position and a second position, based on the position of the body portion of the subject. One or more sensor units are communicably coupled to the positioning system. One or more sensor units are configured to monitor position of the body portion of the subject. The positioning system is configured to operate between the first position and the second position based on the readings monitored by each of the at least one sensor unit. In one configuration, it is optional to have one or more sensor units as part of the equine MRI system. An alternative is to have an operator triggering the positioning system for the Magnetic Field Assembly to retract or rise. A computing device is communicably coupled to the retractable magnet assembly and configured to monitor the imaging of the body portion. The same or another computing device is configured to process the magnetic field interaction of the body portion positioned in the bore of the magnet for generating a visual representation of an anatomy of the body portion.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

OVERVIEW

Various embodiments of the present disclosure provide a vertically retractable Magnet Field Assembly for a Magnetic Imaging Resonance (MRI) system. The MRI Magnet Field Assembly includes a magnet and is configured to have a bore for receiving a body portion of a subject such as, but is not limiting to, a horse. The bore extends along a longitudinal axis of the magnet and defines an inner surface of the magnet. At least one flux generating element is disposed within the magnet such that, each of the at least one flux generating element surrounds the bore. Each flux generating element is configured to generate a magnetic field, for imaging the body portion positioned within the bore. The flux generating elements may also be made of superconducting material. As such, the magnet may be fluidically coupled to a cooling unit, for maintaining cryogenic temperature conditions within the magnet. The cryogenic temperature conditions enable superconductivity for each of the flux generating elements. A gradient coil is mounted to the inner surface of the magnet and extends along the length of the bore. The gradient coil is configured for spatial encoding by altering the main magnetic field in a spatially specific pattern per gradient control signal to differentiate signal from different location of the body portion. Further, a transmit coil may be mounted onto an exposed circumferential surface of the gradient coil and extends along the length of the gradient coil. The transmit coil is configured to transmit RF pulse rotating net magnetization away from its alignment with the main magnetic field. In one configuration, it is optional to have a transmit coil as part of the retractable Magnet Field Assembly. An alternative is to not to mount a transmit coil on the retractable Magnet Field Assembly and instead have a transmit coil located local to receive coils. A magnet shielding element is also mounted to a bottom portion of the magnet. The magnet shielding element is configured to attenuate a fringe field generated by the primary flux generating element. In one configuration, it is optional to have a magnet shielding element as part of the retractable Magnet Field Assembly.

The term "vertically retractable" herein means that the Magnet Field Assembly can move from an upward raised position to a downward retracted position, and vice versa. The change in position involves change in height and does not have to be strictly vertical motion. The change in height can be at an angle, can be accelerated, can consists of one or multiple moves. The upward raised position can be an imaging position for a standing animal or human. The retracted position is such that a standing animal or human can safely move, or walk, to or away from the Magnet Field Assembly or imaging position and that the Magnet Field Assembly in the retracted position may or may not be fully flush with the floor.

The present disclosure also provides an MRI system or an equine MRI system employing the retractable Magnet Field Assembly and the positioning system as described below.

The movement of the retractable Magnet Field Assembly is achieved by a positioning system coupled to the magnet. The positioning system is configured to manoeuvre the magnet in at least one coordinate axes between a first position and a second position. The positioning system may be communicably coupled or associated with at least one sensor unit, which is configured to monitor position of the body portion of the subject. The positioning system, thus, operates suitably, based on the readings provided by the sensor unit.

The positioning system includes a motion controller computing unit associated suitably with the magnet, the positioning system and the sensor unit. The motion controller computing unit is configured to selectively move the magnet to accommodate the motion of the body portion. The same, or a separate, computing unit is configured to process a magnetic field interaction between the body portion and the magnet assembly, for generating a visual representation of an anatomy of the body portion. The motion controller computing unit is also configured to selectively operate the positioning system based on the readings or signals received from the sensor unit. The motion controller computing unit operates the positioning system so that the magnet may be positioned suitably for receiving the body portion of the subject.

This configuration of the present invention provides a compact magnet assembly which can be a cryogen-free "dry" superconducting magnet. That is, the compact magnet assembly of the present invention mitigates the need for using liquid helium for maintaining the cryogenic temperature conditions within the system. As such, the magnet assembly of the present disclosure eliminates the shortcomings associated with the use of liquid helium in the MRI system. Additionally, the magnet assembly is also simple in construction, inexpensive in operation and maintenance.

Various embodiments of a retractable magnet assembly for a Magnetic Resonance Imaging (MRI) system are explained in a detailed manner, herein with reference to FIG. 1 to FIGS. 8A and 8B.

Figure 1:
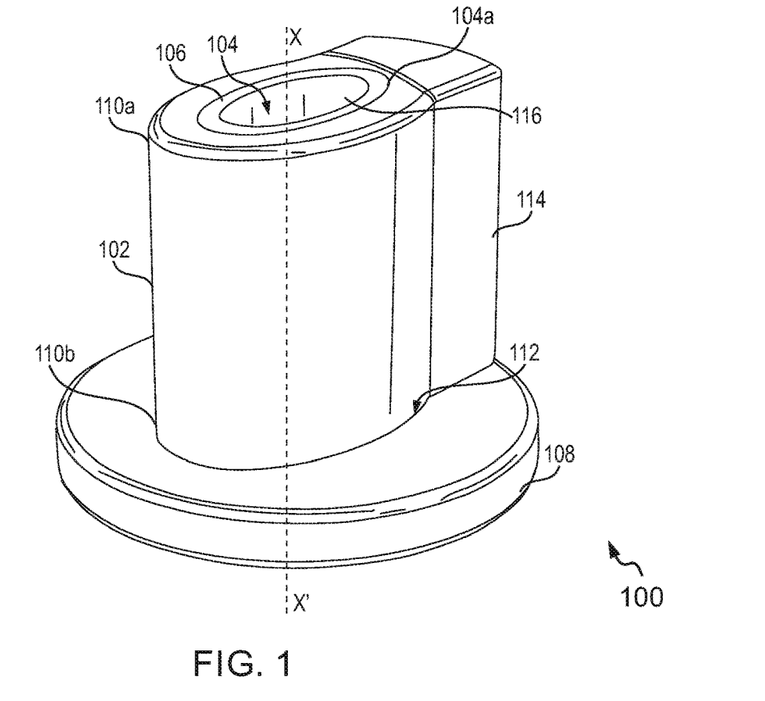
FIG. 1 is a schematic view of a retractable Magnet Field Assembly for a Magnetic Imaging Resonance (MRI) system, in accordance with an example embodiment of the present disclosure.

FIG. 1 in one exemplary embodiment of the present disclosure, illustrate a retractable Magnet Field Assembly 100 (hereinafter referred to as 'assembly 100') for a Magnetic Resonance Imaging (MRI) system (referenced as '700' in FIG. 7). The assembly 100 can be adapted to be a compact assembly, thereby mitigating the need for using liquid helium therein.

The Magnet Field Assembly 100 includes a magnet 102. The magnet 102 may be a cylindrical structure of a unibody construction or a fabrication of a plurality of segments, configured to support components of the magnet assembly 100. The magnet 102 includes a bore 104 extending along a longitudinal axis X-X' and configured for receiving a body portion (for e.g., referenced as 404 in FIGS. 4A-4D) of a subject (for e.g., referenced as 402 in FIGS. 4A-4D. The bore 104 is configured to enable positioning of the body portion 404 suitably within the magnet 102, while also ensuring balance or posture of the subject 402 upon insertion of the body portion 404 within the bore 104. As such, the bore 104 is dimensioned corresponding to the dimensions of the body portion 404 to be positioned therein. A clearance (not shown in the Figures) may be considered in the dimensions of the bore 104 for comfort of the subject 402, upon insertion of the body portion 404 within the bore 104, as per design feasibility and requirement. In one implementation, the shape and configuration of the bore 104 may be selected based on the body portion 404 inserted therein. In one configuration, the shape of the bore 104 may be selected to one of a circular shape, an elliptical or elongated shape, a rectangular shape or any other shape as per design feasibility and requirement.

In one implementation, the bore 104 extends along the entire length of the magnet 102, thereby forming an opening therein. In another implementation, the bore 104 may extend up to a predetermined or required length along the longitudinal axis X-X'.

In an embodiment, the subject 402 may be a horse and the body portion 404 may be a limb of the horse. As such, the bore 104 may be configured such that, size of the bore 104 at a top portion 110a of the magnet 102 is greater than the bore size at the bottom portion 110b of the magnet 102. This configuration of the bore 104 conforms to the shape of the limb of the horse. In another configuration, the bore 104 may be elongated along a cranial-caudal direction of the limb of the horse relative to a medial-lateral direction of the limb of the horse. In one configuration, the bore 104 may be configured with a uniform cross-section. In another configuration, the bore 104 may be configured with a varying cross-section, based on the configuration of the body portion 404. In one configuration, the magnet 102 may be configured with a uniform cross-section. In another configuration, the magnet 102 may be configured with a varying cross-section, based on the configuration of the body portion 404.

Figure 2A:
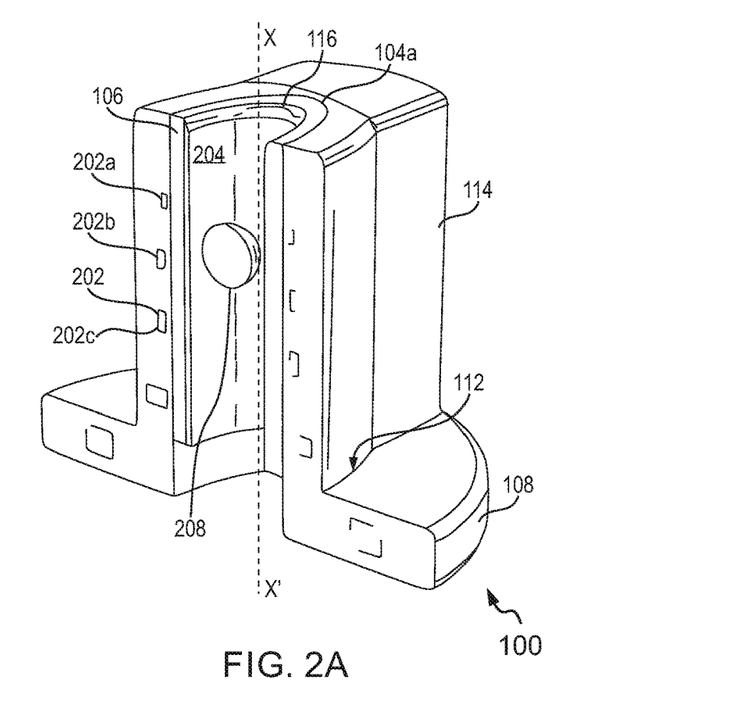
FIG. 2A is a cross-sectional view of the assembly of FIG. 1, in accordance with an example embodiment of the present disclosure.
Figure 2B:
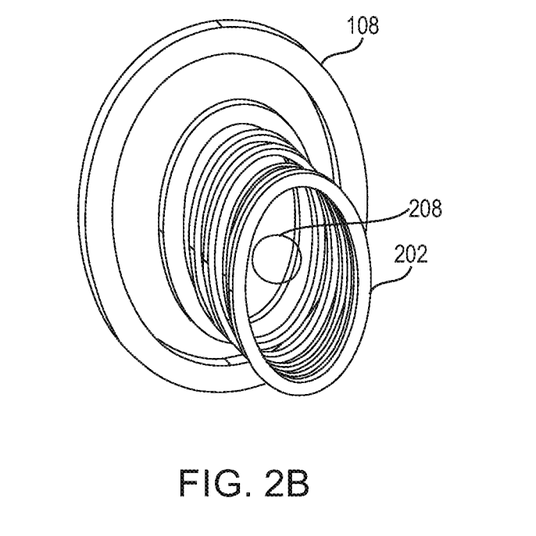
FIG. 2B is a schematic view of the flux generating element arrangement in the magnet of the assembly of FIG. 1, in accordance with another example embodiment of the present disclosure.

Referring to FIG. 2A in conjunction with FIG. 1, at least one flux generating element 202 (collectively referred for 202a, 202b, . . . 202c) is disposed within the magnet 102. The at least one flux generating element 202 (hereinafter referred to as 'flux generating element 202') is disposed such that, the each of the flux generating element 202 (for e.g., flux generating element 202a) surrounds the bore 104 within the magnet 102. The flux generating element 202 is configured to generate magnetic field for magnetizing the body portion 404 positioned in the magnet 102. In one implementation, the flux generating element 202 is typically located about an imaging region 208 or a field of view (FOV) 208 of the magnet 102. The imaging region 208 may be the region at which the magnetic field emanating from the flux generating element 202 are channeled to form a uniform field, to enable uniform magnetization of the body portion 404. Consequently, enabling high-quality visual representation of the body portion 404 of the subject 402. The imaging region 208 may be located closer to the top of the magnet assembly 100 as shown in FIG. 2A. In one implementation, the FOV 208 may alter based on the body portion 404 of the subject 402 to be imaged or the configuration of the magnet assembly 100.

In one configuration, for the unibody construction of the magnet 102, support members (not shown in Figures) may be configured within the magnet 102 for holding the flux generating element 202. The support members may lock the flux generating element 202 in place by suitable locking means as per feasibility and requirement. In another configuration, for the fabricated construction of the magnet 102 (not shown in Figures), the flux generating element 202 may be locked in the required position via the support members and thereafter assembled to form the magnet 102.

In one implementation, the flux generating element 202 includes flux generating elements 202a, 202b and 202c (for e.g., as shown in FIG. 2A). In these scenarios, the flux generating elements 202 are offset to each other by a pre-determined distance, to prevent losses that may associated due to interaction of magnetic fields generated by each of the flux generating element 202. In another implementation, the flux generating elements 202a, 202b and 202c may be stacked with one another suitably.

In one configuration, the flux generating element 202 may be a single flux generating element, which extends along the length of the bore 104 (not shown in Figures). Thus, in this scenario, the flux generating element 202 may be a cylindrical structure with a spiral coil configuration, which extends from the top portion 110a to the bottom portion 110b of the bore 104. The configuration of the flux generating element 202 in these scenarios, i.e., the pitch between each turn of the flux generating element 202 and orientation of each turn (not shown in Figures) may be selected as per design feasibility and requirement.

Figure 8A:
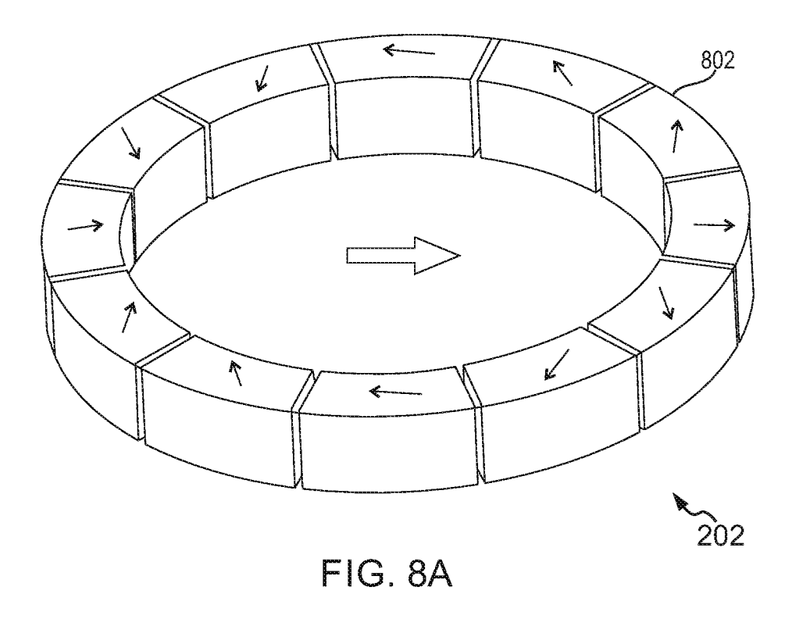
FIG. 8A is a schematic view of the flux generating element disposed in the magnet, in accordance with an example embodiment of the present disclosure.
Figure 8B:
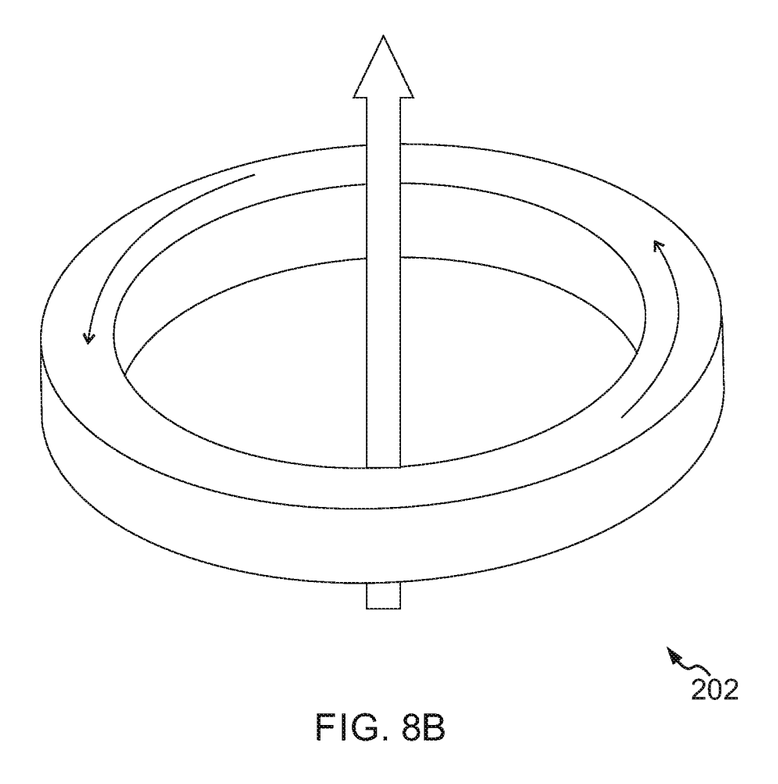
FIG. 8B is a schematic view of the flux generating element disposed in the magnet, in accordance with another example embodiment of the present disclosure.

In an embodiment, the flux generating element 202 may be made of a magnetic material, such as but not limited to, Neodymium Iron Boron (NdFeB), of required or sufficient magnetic field strength. In an embodiment, the magnet material may be arranged in a Halbach magnet array 800 (for e.g. as shown in FIG. 8A). In these scenarios, the flux generating element 202 may be magnetized in the required direction, based on the direction of flow of magnetic field, prior to its disposal within the magnet 102. The magnetization of the flux generating element 202 be carried out via conventional techniques, i.e., by introducing a magnetic field of required intensity or any other techniques as per feasibility and requirements. This configuration ensures that a uniform magnetic field impinges onto the body portion 404 during use of the assembly 100, thereby ensuring a high-quality visual representation of the anatomy of the body portion 404. In one configuration, the Halbach magnet array 800 may be fabricated by joining a plurality of segments 802 of magnetic material via conventional mounting techniques. The shape and configuration of the Halbach magnet array 800 may be selected based on the design feasibility and requirement. In another configuration, the flux generating element 202 may be a current loop flux generating element (for e.g. as shown in FIG. 8B).

In an embodiment, the flux generating element 202 may be a superconducting coil. In other words, the flux generating element 202 may be made of a superconducting material, such as but not limited to, metals, ceramics, doped semiconductors or any other materials as per requirement. In this scenario, the flux generating element 202 is required to be maintained at a temperature below a critical temperature, for invoking superconductivity. As such, a cooling unit (referenced as '114' in FIG. 1) is configured in the assembly 100 for cooling the flux generating element 202 below the critical temperature. The critical temperature of the superconducting material may be the temperature at which the superconductivity property of the material is invoked. The aspect of the cooling unit 114 is explained in the subsequent paragraph of the description.

Referring back to FIG. 1, a cooling unit 114 is mounted to the magnet 102 for maintaining the temperature of the flux generating element 202 below the critical temperature, during operation. The cooling unit 114 may be configured to route a suitable refrigerant within the cooling unit 114 for maintaining temperature of the flux generating element 202. The refrigerant may be routed via a suitable pipeline to a heat exchanger or cryocompressor (not shown in Figures). The cooling unit 114 may be selected to be one of a cryocooler system or any other system, configured for maintaining the temperature of the flux generating element 202. In one embodiment, the flux generating element 202 is cooled with liquid helium. Another embodiment uses cryogen-free cooling configuration, "dry" superconducting magnet cooling. Consequently, mitigating the equipment required for maintenance and safety of the liquid helium within the magnet 102, making the assembly 100 compact and simple in construction. In one configuration, the cooling unit 114 may be mounted along a circumferential surface of the magnet 102. In another configuration, the cooling unit 114 may be mounted at any location within the magnet 102, as per requirement.

Further, the assembly 100 includes a gradient coil 106 mounted onto an inner surface 104a of the magnet 102 defined by the bore 104. The gradient coil 106 is configured to extend along a length of the bore 104. The gradient coil 106 is configured for spatial encoding by altering the main magnetic field in a spatially specific pattern per gradient control signal to differentiate signal from different location of the body portion 404 during imaging. The spatial encoding results in determination of RF signal location in coordinate axes. The spatial encoding, thus, enables to determine the location of the RF signal generated by the body portion 404. The shape of the gradient coil 106 may follow the shape of the bore 104, so the gradient coil 106 may be non-circular in shape. For example, the gradient coil 106 may be elliptical in cross section or other shape similar to the shape of the bore 104, and may have a varying cross section along longitudinal axis X-X', similar to the bore shape.

Referring to FIG. 2A in conjunction with FIG. 1, the assembly 100 may also include a transmit coil 204 mounted onto an exposed circumferential surface 116 of the gradient coil 106 and extending along a length of the gradient coil 106. In this case, the transmit coil 204 may follow the shape of the bore 104 and can be non-circular in shape. Alternatively, the transmit function may be performed by the Radio Frequency coil attached to the body part being imaged operated in transmit/receive mode. The transmit coil 204 is configured to transmit a Radio Frequency (RF) field to the body portion 404 of the subject 402 positioned within the bore 104. The RF pulse rotates the net magnetization of the hydrogen protons of the body portion 404 subjected within the bore 104.

Referring back to FIG. 1, the assembly 100 further includes a magnet shielding element 108 mounted to the bottom portion 110b of the magnet 102. In one configuration, the magnet shielding element 108 is particularly, mounted to a circumferential side surface 112 of the bottom portion 110b, thereby forming a T-shaped profile. The magnet shielding element 108 is configured to attenuate a peripheral magnetic field (or fringe field) emanating outside the magnet 102 of the magnet assembly 100. The magnet shielding element 108 may be configured with the unibody structure mounted to the circumferential side surface 112 or may be fabrication of segments mounted around the circumferential side surface 112. In one configuration, the magnet shielding element 108 has a superconducting coil typically employed in traditional MRI scanners for attenuating the peripheral magnetic field. The magnet shielding element 108 may be located outside the region of the body portion 404 of the subject 402, i.e., the magnet shielding element 108 mounted to the bottom portion 110b may not interfere with the body portion 404 of the subject 402.

Figure 3A:
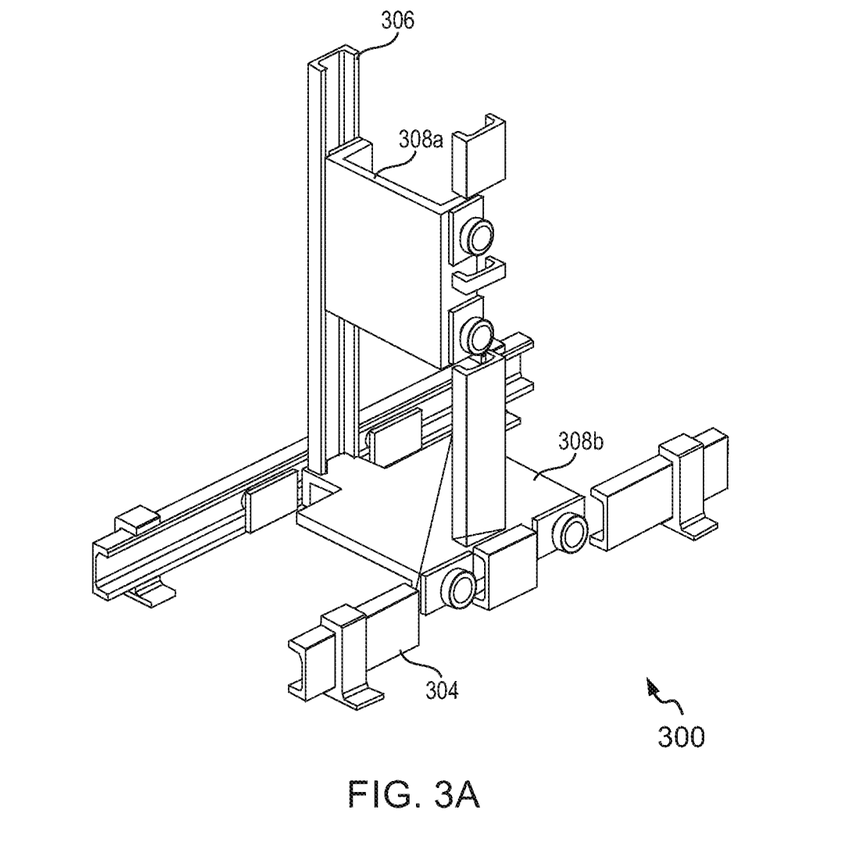
FIG. 3A illustrates a schematic view of a positioning system for a Magnetic Imaging Resonance (MRI), in accordance with an example embodiment of the present disclosure.
Figure 3B:
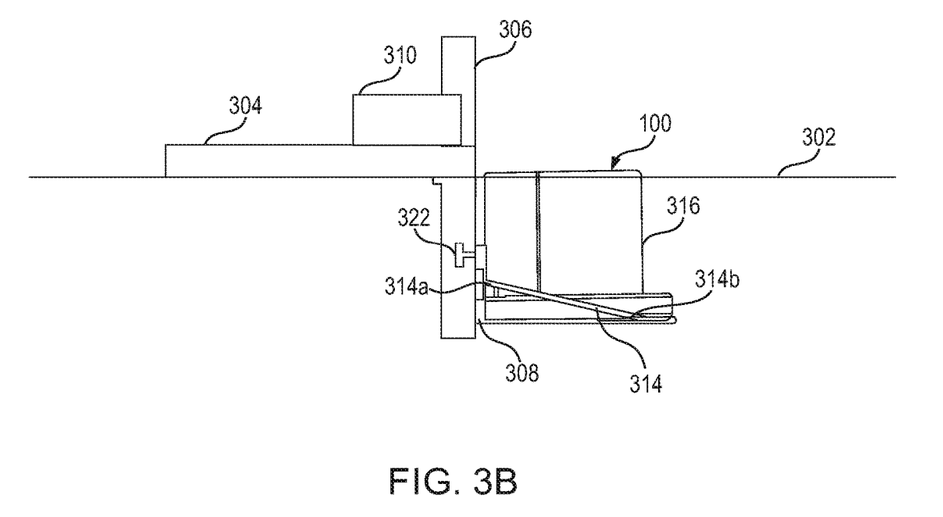
FIG. 3B is a schematic view of the positioning system, in accordance with another example embodiment of the present disclosure.
Figure 3C:
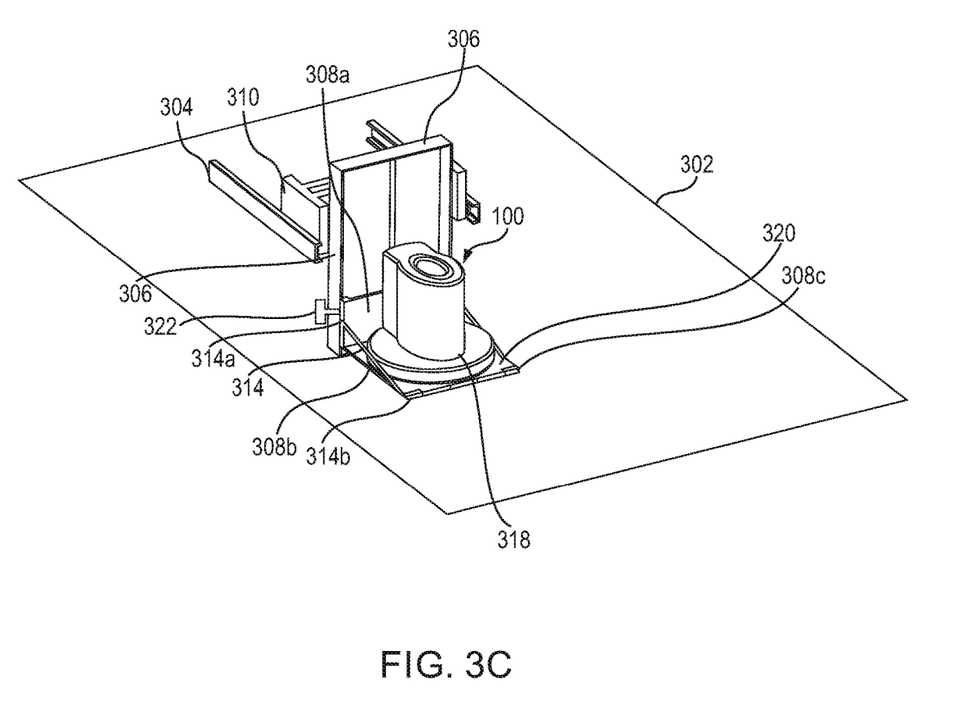
FIG. 3C is a schematic view of the positioning system in accordance with another example embodiment of the present disclosure.

Further, the assembly 100 is mounted to a positioning system 300 (for e.g., as shown in FIGS. 3A, 3B and 3C). The positioning system 300 is configured to manoeuvre the magnet assembly 100 in at least a coordinate axis suitably, for positioning the body portion 404 therein, which is further explained in detail.

FIGS. 3A-3C in one exemplary embodiment of the present disclosure, illustrate a schematic view of the positioning system 300 mounted to the assembly 100. The positioning system 300 is configured to manoeuvre the magnet assembly 100 between a first position 316 (for e.g., as shown in FIG.

Figure 4A:
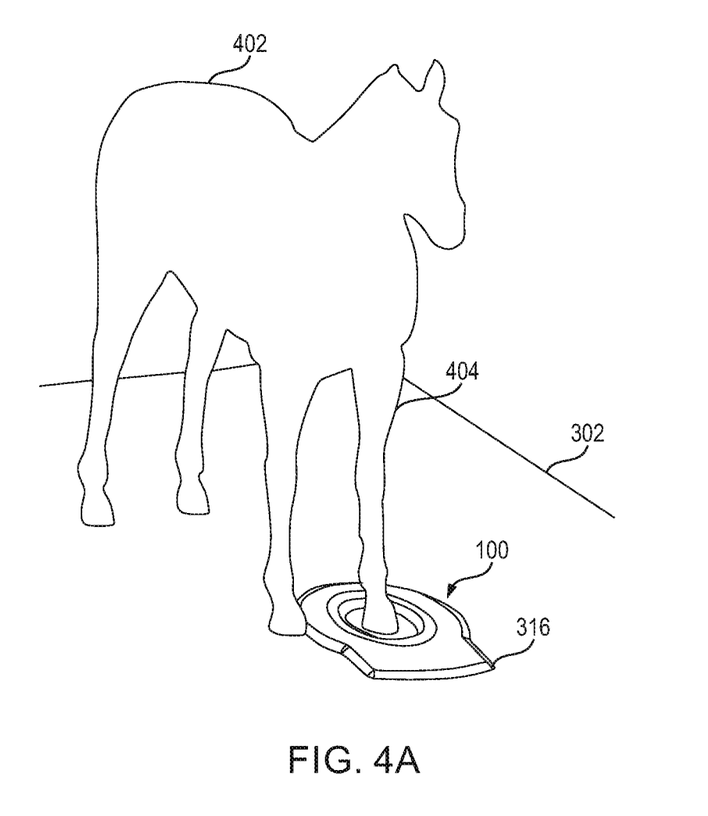
FIG. 4A is a schematic view of the Magnet Field Assembly retracted into the floor allowing movement of a subject, in accordance with an example embodiment of the present disclosure.
Figure 4B:
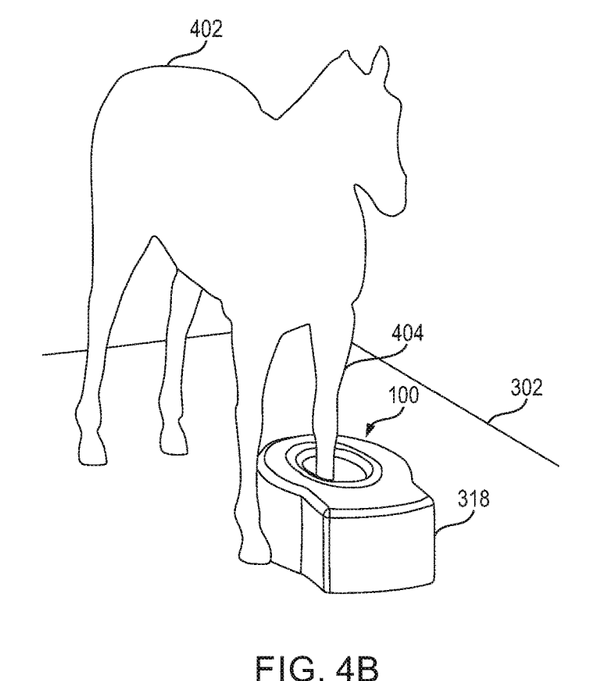
FIG. 4B is a schematic view of the Magnet Field Assembly in use for scanning a region of interest of the subject, in accordance with another example embodiment of the present disclosure.
Figure 4C:
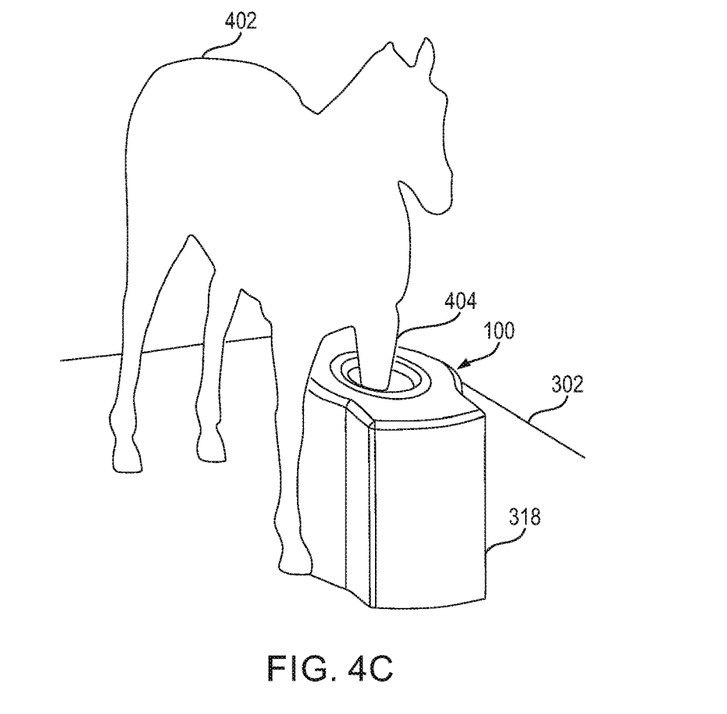
FIG. 4C is a schematic view of the Magnet Field Assembly in use for scanning another region of interest of the subject, in accordance with another example embodiment of the present disclosure.

3B and FIG. 4A) and a second position 318 (for e.g., as shown in FIG. 3C and FIG. 4B) suitably. The first position 316 may be a resting or a retracted position of the assembly 100. In the first position 316, assembly 100 is retracted to the floor member 302 until assembly 100 is flush with the floor member 302 or assembly 100 is retracted to the point that the subject 402 or the animal can safely step out of the bore 104. As such, in the first position 316 the assembly 100 may be retracted within a cavity (not shown in Figures) configured to a floor member 302 (for e.g., as shown in FIG. 3B). The second position 318 may be an operative position or an extended position above the floor member 302 and which is oriented based on the position of the body portion 404, so that the subject 402 may insert the body portion 404 into the magnet 102. In another implementation, the second position 318 may be the operative position that is aligned based on the position of the body portion 404, so that the assembly 100 is operated further and allow the magnet 102 to automatically surround a resting or a lateral recumbent position subject 402. Thus, for operating the assembly 100 between the first position 316 and the second position 318 suitably, the positioning system 300 is employed.

The positioning system 300 includes a support structure 308 mounted to the magnet 102, via conventional mounting means, such as but not limited to, fastening and the like. The support structure 308 acts as a platform for maneuvering the assembly 100 between the first position 316 and the second position 318. The support structure 308 is further coupled to a first guide rail 304 mounted to the floor member 302 and oriented horizontally. The support structure 308 maybe coupled to the first guide rail 304 via rollers or any other suitable means to enable movement along the first guide rail 304. As such, the first guide rail 304 enables a horizontal movement or movement in a x-direction (as illustrated in the Figures) of the assembly 100.

The positioning system 300 further includes a second guide rail 306 configured to extend laterally with respect to the first guide rail 304. As such, the second guide rail 306 may form an L-shaped structure or a T-shaped structure, based on the location of the extension with the first guide rail 304. The second guide rail 306 is configured to allow a vertical movement or movement in a z-direction (as illustrated in the Figures) of the assembly 100.

Further, the positioning system 300 includes a third guide rail 310 which may extend either from the first guide rail 304 or the second guide rail 306. The third guide rail 310 is configured to allow movement of the assembly 100 in a y-direction (as illustrated in the Figures). Thus, the combination of the first guide rail 304, the second guide rail 306 and the third guide rail 310 is configured to cover translational motion or movement of the assembly 100 suitably.

Figure 4D:
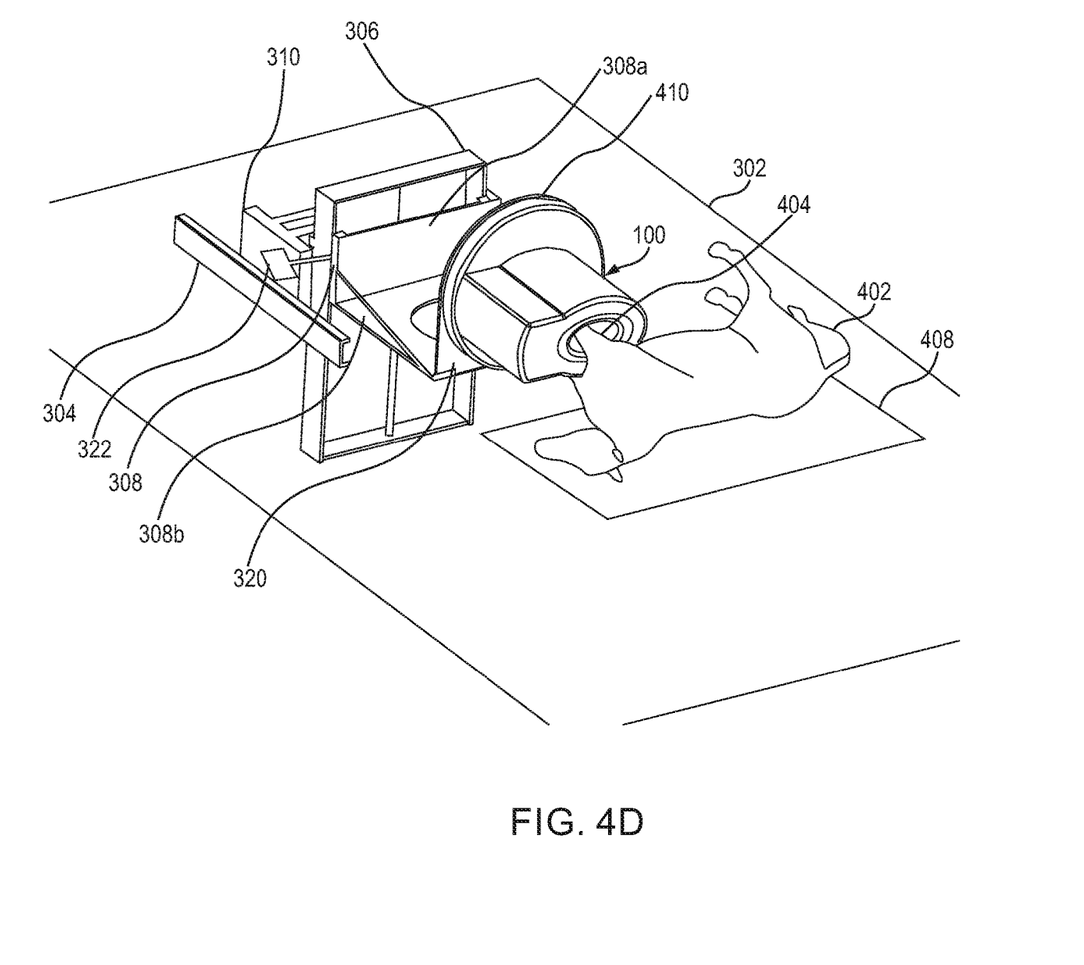
FIG. 4D is a schematic view of the Magnet Field Assembly in use for scanning a region of interest of the subject in the sleeping position or a lateral recumbent position, in accordance with another example embodiment of the present disclosure.

In one configuration, the support structure 308 may comprise a base member 308a and a frame member 308b (for e.g., shown in FIG. 3A). The base member 308a is movably mounted to the second guide rail 306 and oriented in laterally to the floor member 302. The frame member 308b extends from the base member 308a and is oriented parallelly to the floor member 302 to form the L-shaped structure. The frame member 308b is configured to receive the assembly 100 (for e.g., as shown in FIGS. 3B and 3C). The base member 308a of the support structure 308 is operable suitably for movement of the second guide rail 306 along the length of the first guide rail 304, i.e., allowing a horizontal movement of the assembly 100 via the second guide rail 306. The frame member 308b of the support structure 308 may be operable for movement along the length of the second guide rail 306. In one implementation, the configuration of the base member 308a and the frame member 308b may alter as per design feasibility and requirement. In another configuration, a plate member 320 (for e.g., as shown in FIG. 3C) is pivotally coupled to an aft end of the frame member 308b via a hinge member 308c (for e.g., as shown in FIG. 3C). The plate member 320 is configured to be mounted to the assembly 100. The plate member 320 is adapted to be pivotally operated for orienting the assembly 100 suitably. A gusset member 314, with a first end 314a slidably mounted to the frame member 308b and the second end 314b pivoted to the base member 308a (for e.g., as shown in FIG. 3C) is provided to support the plate member 320. Thus, the configuration of the plate member 320 provides additional degree of control to the manoeuvrability of the assembly 100. In one configuration, a free end 410 (as shown in FIG. 4D) of the plate member 320 may be locked onto the frame member 308b via conventional locking means, when the assembly 100 is in the level or in an un-tilted position. This configuration ensures greater control for the positioning system 300 over maneuverability of the assembly 100.

The positioning system 300 also includes a drive mechanism 322 (for e.g., shown in FIGS. 3B and 3C) coupled to the support structure 308. The drive mechanism 322 is associated with a computing unit (referenced as '702' in FIG. 7), which is configured to actuate the drive mechanism 322 for operating the support structure 308. As such, the drive mechanism 322 is configured to selectively operate the support structure 308 in the first guide rail 304, the second guide rail 306 and the third guide rail 310 for adjusting position of the assembly 100 in the coordinate axes. In one configuration, the drive mechanism 322 may be a feed screw driven by a motor, a geared track driven by a motor with a gear drive, or an actuator and the like as per the design feasibility and requirements. The operation of the positioning system 300 via the drive mechanism 322 is explained as an example in description pertaining to FIGS. 4A to 4C.

Figure 5:
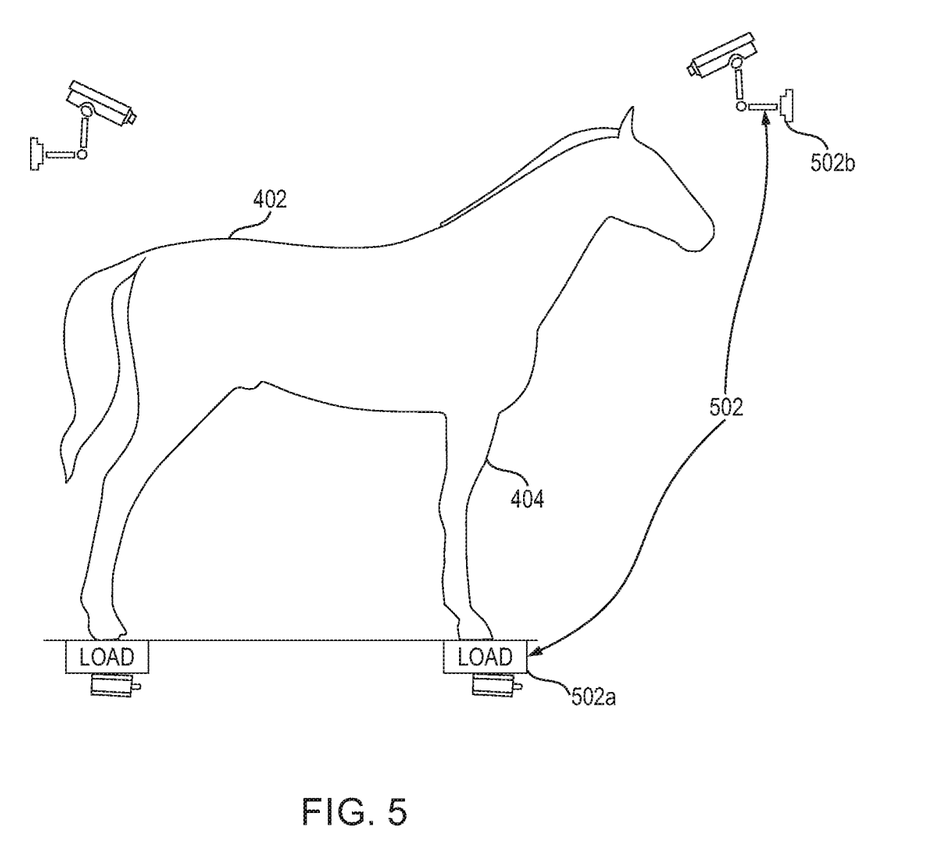
FIG. 5 is a schematic view of the assembly integrated with at least one sensing unit, in accordance with an example embodiment of the present disclosure.

Further, the positioning system 300 is communicably coupled to at least one sensing unit 502 (for e.g., as shown in FIG. 5). The sensing unit 502 is configured to monitor position of the subject 402 and/or the body portion 404 of the subject 404. In one configuration, the sensing unit 502 may be a load cell unit 502a mounted beneath the floor member 302. The load cell unit 502a is configured to measure the load exerted by the subject 402 while resting on the floor member 302. As such, when the subject 402 is moving, a variation in the load is sensed by the load cell unit 502a. Upon sensing the variation in the load, the motion controller computing unit actuates the drive mechanism 322 to operate the assembly 100 to the first position 316 when the assembly 100 is in the second position 318. This configuration, acts as a safety precaution, allowing the subject 402 to move freely without the assembly 100 acting as an obstruction, which may lead the subject 402 to fall or cause an accident. In one implementation, multiple units of the load cell unit 502a may be mounted across the floor member 302 for accurate determination of the variation of the load in the event of movement of the subject 402 during magnetization. In another implementation, the sensing unit 502 may also be a camera unit or a motion sensor 502b oriented to monitor the movement of the subject 402. When the camera unit 502b detects a movement of the subject 402 during the magnetization, the motion controller computing unit (not shown in the figures) actuates the drive mechanism 322 to operate the assembly 100 to the first position 316 when the assembly 100 is in the second position 318.

Further, multiple camera units 502b may be oriented to monitor the movement of the subject 402.

In one implementation, time period taken by the drive mechanism 322 for operating the assembly 100 to the first position 316 from the second position 318, may be in the range of about 250 milliseconds to about 500 milliseconds. In another configuration, for effective working, the magnet assembly 100 may be retracted to the floor member 302 at a faster rate which may be approximately 250 milliseconds. In yet another configuration, 500 milliseconds may be the time an object may take to free fall from about 1 meter in height, so there is need of 2 to 3 times the acceleration of gravity to retract the magnet assembly 100.

FIGS. 4A-4D in one exemplary embodiment of the present disclosure, illustrate the assembly 100 employed for scanning the body portion 404 of the subject 402. In one implementation, the subject 402 is an equine, such as a horse and the body portion 404 to be scanned is a limb of the horse.

Prior to the initiation of the scanning procedure, the horse may be sedated by a medical practitioner (not shown in Figures) and is positioned on the floor member 302 of a platform. The horse may either be in a standing position or in a sleeping position. The assembly 100 is initially in a retracted position (e.g., the first position 316 of FIG. 3B). In the retracted position, the assembly 100 may be in flush configuration with the floor member 302. At this position, the horse is positioned on the floor member 302 such that the limb to be scanned is placed in the vicinity of the bore 104 of the magnet assembly 100 (for e.g., as shown in FIG. 4A). In this scenario, the drive mechanism 322 is operated to adjust position of the magnet 102 via the positioning system 300 suitably, so that the bore 104 is aligned with the limb of the horse. Upon aligning the magnet 102, the drive mechanism 322 erects the assembly 100 from the first position 316 to the second position 318 (for e.g., as shown in FIG. 4B), by actuating the support structure 308 along the second guide rail 306. The second position 318 may be adjusted based on area of the limb to be scanned or magnetized.

In another implementation, when the horse is in the sleeping position or a lateral recumbent position on a gurney 408 (for e.g. as shown in FIG. 4D), the second position 318 as illustrated in FIG. 4B may not be feasible. In one configuration, at this position of the horse, a support member or a bracket (not shown in Figures) may be placed to ensure separation between the limbs. In this scenario, the drive mechanism 322 is operated based on the orientation of the limb of the horse. For this implementation, the positioning system 300 may be embedded with sensors, for adjusting orientation of the assembly 100 based on the position of the limb. Thus, in the position of the limb as shown in FIG. 4B, the drive mechanism 322 may initially operate the support structure 308 vertically (i.e. in the z-direction), to align with the vertical position of the limb. Thereafter, the support structure 308 is operated in the y-direction to align with the position of the limb. In this scenario, the plate member 320 is actuated by the drive mechanism 322 to tilt the assembly 100 to align the bore 104 with the limb. At this position, the drive mechanism 322 may operate the support structure 308 in the x-direction to enable insertion of the limb into the magnet 102, for scanning of the limb.

Figure 6:
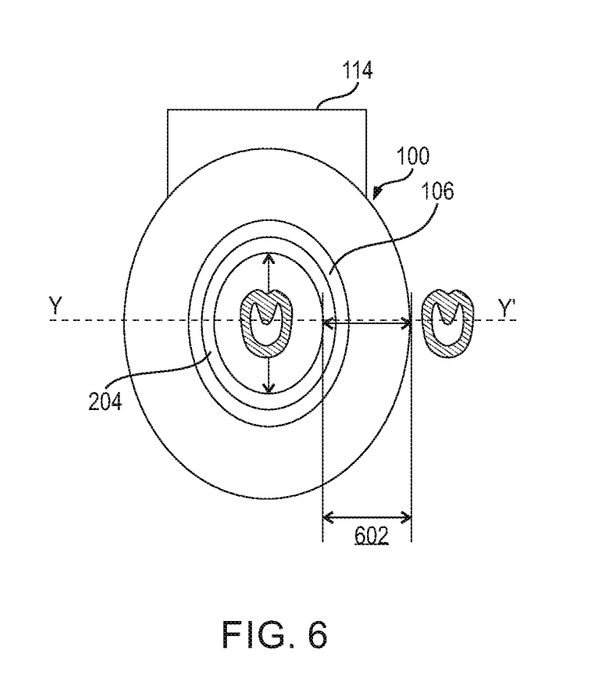
FIG. 6 is a schematic view of the Magnet Field Assembly depicting a thickness factor of a magnet of the assembly, in accordance with an example embodiment of the present disclosure.

In one configuration, the drive mechanism 322 may adjust the position of the assembly 100 during insertion of the limb of a conscious standing horse into the magnet 102, based on a thickness factor 602 (for e.g., as shown in FIG. 6). The thickness factor 602 of the magnet 102 may be the combined thickness of the magnet 102, the gradient coil 106 and the transmit coil 204 along a lateral axis Y-Y' (for e.g., as shown in FIG. 6). Further, the thickness factor 602 also defines the maximum thickness that the size and configuration of the magnet assembly 100 may be selected for scanning a subject 402, based on the size of the body portion 404. Typically, the horse while standing naturally tends to keep its feet together, which may be approximately 7 inches or 177.8 mm apart laterally. Thus, the thickness factor 602 is required to be less than 7 inches for enabling use of the magnet assembly 100 for scanning the limbs of a conscious standing horse. The thickness factor 602 may also be a central pole thickness of the assembly 100.

Figure 7:
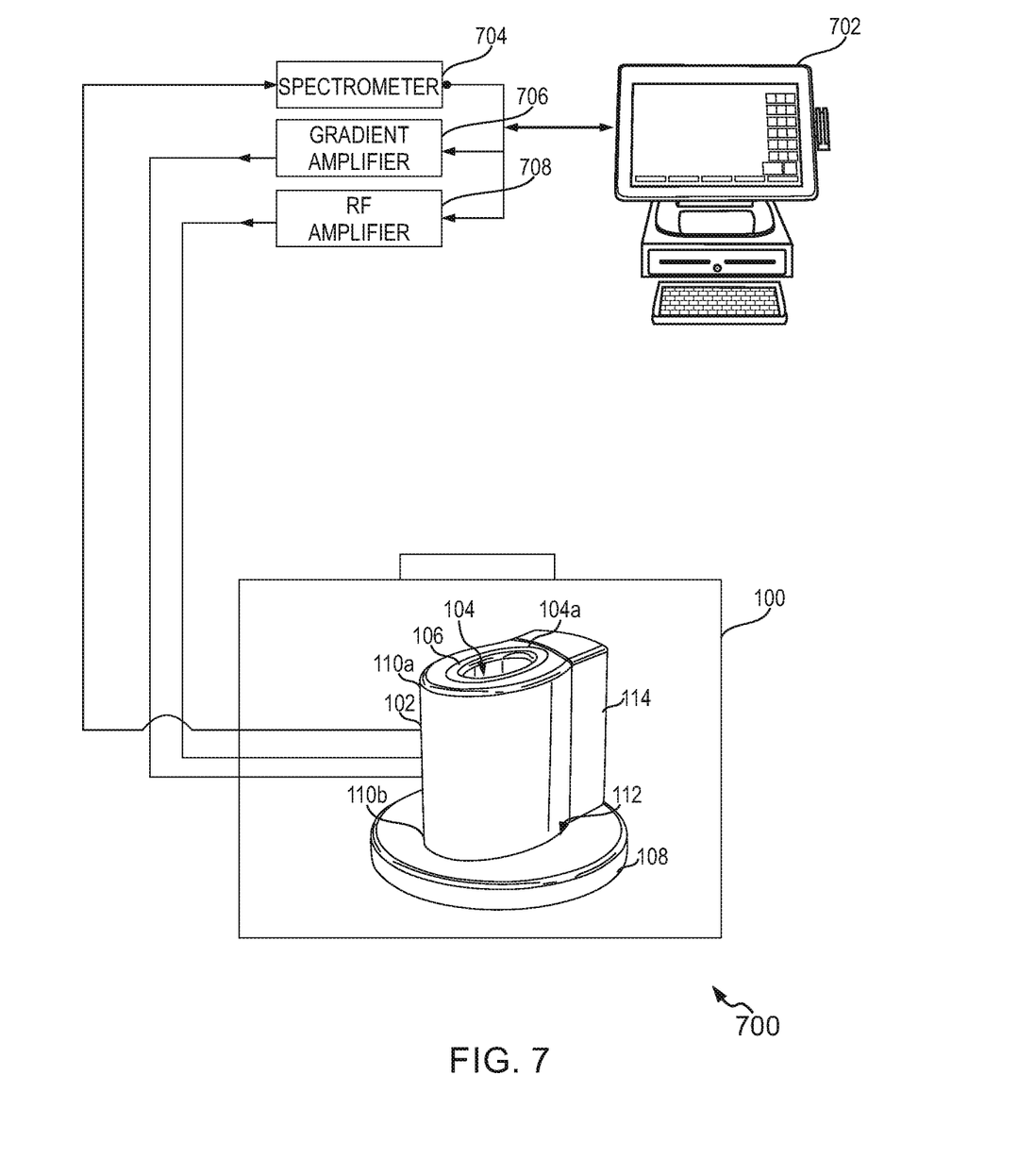
FIG. 7 is a schematic view of an equine MRI system employing the Magnet Field Assembly, in accordance with an example embodiment of the present disclosure.

FIG. 7 in one exemplary embodiment of the present disclosure illustrates a schematic view of an equine MRI system 700, employing the vertically retractable Magnet Field Assembly 100. The system 700 is configured to monitor and react to the movement of the body portion 404 and generate the visual representation of the anatomy of the body portion 404. The system 700 is configured to operate assembly 100 along with the positioning system 300 and the sensing unit 502, as per conventional MRI systems.

The MRI system 700 includes a computing device 702 connected to the assembly 100, via a spectrometer 704, a gradient amplifier 706 and an RF amplifier 708. The spectrometer 704, the gradient amplifier 706 and the RF amplifier 708 are suitably configured for the assembly 100, for generating, transmitting gradient and RF waveforms and receiving signals during imaging of the body portion 404. As such, the gradient amplifier 706 is configured to optimize the performance of the gradient coil 106. The RF amplifier 708 may be configured to work with the transmit coil, while the spectrometer 704 may generate the waveforms and receive signals from the body portion 404. The computing device 702 may be configured to control operations of the assembly 100 and operate the assembly 100 suitably via the positioning system 300 and the sensing unit 502 as already described in description pertaining to FIGS. 2A, 2B, 3A-3C and 4A-4D. Upon receiving the signals, the computing device 702 may process and/or manipulate the signals suitably for generating the visual representation.

In an embodiment, the body portion 402 that may be subjected for imaging and consequently for generating the visual representation (i.e. the imaging regions in the horse) may be a knee, a hock, a pastern, a hoof and a fetlock of the horse.

In one embodiment, the Magnet Field Assembly 100 may also be employed in the traditional MRI system for scanning the body portion 404.

The benefits and advantages described above may relate to one embodiment or may relate to several embodiments. The embodiments are not limited to those that solve any or all of the stated problems or those that have any or all of the stated benefits and advantages.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:

1. A vertically retractable magnet assembly for a Magnetic Imaging Resonance (MRI) system, wherein the magnet assembly is capable of moving from an upward raised position for imaging to a downward retracted position to allow a subject to move safely, the assembly comprising:

a magnet configured with a bore for receiving a body portion of the subject, the bore defining an inner surface of the magnet and extending along a longitudinal axis of the magnet, the magnet comprising at least one flux generating element disposed within the magnet and oriented such that each of the at least one flux generating element surrounds the bore, wherein, each of the at least one flux generating element is configured to generate a magnetic field for magnetizing the body portion positioned within the bore to generate a visual representation of an anatomy of the body portion, and wherein the magnet is coupled to a positioning system, the positioning system configured to adjust position of the magnet in at least a coordinate axis between a first position and a second position; and at least one sensor unit communicably coupled to the positioning system, the at least one sensor unit configured to monitor position of the body portion, wherein the positioning system is configured to operate between the first position and the second position based on readings monitored by each of the at least one sensor unit.

2. The assembly as claimed in claim 1, wherein the bore of the magnet is noncircular in shape and oriented perpendicularly to the longitudinal axis of the magnet.

3. The assembly as claimed in claim 1, wherein each of the at least one flux generating element is made of a superconducting material, each of the at least one flux generating element maintained at a cryogenic temperature condition via a cooling unit coupled to the magnet, to enable super-conductivity.

4. The assembly as claimed in claim 1, further comprising a gradient coil mounted to the inner surface and extending along a length of the bore, the gradient coil is configured for spatial encoding of the magnetic field and is vertically retractable along with the magnet.

5. The assembly as claimed in claim 4, wherein the gradient coil is of a non-circular shape.

6. The assembly as claimed in claim 4, further comprising a transmit coil mounted onto an exposed circumferential surface of the gradient coil and extending along a length of the gradient coil, the transmit coil configured to transmit Radio Frequency (RF) pulse rotating net magnetization away from its alignment with main magnetic field.

7. The assembly as claimed in claim 6, wherein the transmit coil is of a non-circular shape.

8. The assembly as claimed in claim 1, further comprising a magnet shielding element mounted around a circumferential side surface of a bottom portion of the magnet, the magnet shielding element configured to attenuate a fringe field generated by the at least one flux generating element.

9. The assembly as claimed in claim 1, wherein the first position is a retracted position of the magnet into a floor member and the second position is a raised position of the magnet above the floor member for imaging the body portion.

10. A vertically retractable magnet field assembly for a Magnetic Imaging Resonance (MRI) system, wherein the magnet field assembly is capable of moving from an upward raised position for imaging to a downward retracted position to allow a subject to move safely, the assembly comprising:

a magnet configured with a bore for receiving a body portion of a subject, the bore defining an inner surface of the magnet and extending along a longitudinal axis of the magnet, the magnet comprising at least one flux generating element disposed within the magnet and oriented such that each of the at least one flux generating element surrounds the bore, wherein, each of the at least one flux generating element is configured to generate a magnetic field for magnetizing the body portion positioned within the bore to generate a visual representation of an anatomy of the body portion, and wherein the magnet is coupled to a positioning system, the positioning system configured to adjust position of the magnet in at least a coordinate axis between a first position and a second position, based on the imaging position of the body portion;

a gradient coil mounted to the inner surface and extending along a length of the bore, the gradient coil configured for spatial encoding of the magnetic field and is vertically retractable along with the magnet and at least one sensor unit communicably coupled to the positioning system, the at least one sensor unit configured to monitor position of the body portion of the subject, wherein the positioning system is configured to operate between the first position and the second position based on the readings monitored by each of the at least one sensor unit.

11. The assembly as claimed in claim 10, wherein the bore of the magnet and the gradient coil bore are non-circular in shape, and are oriented perpendicularly to the longitudinal axis of the magnet.

12. The assembly as claimed in claim 10, wherein each of the at least one flux generating element is made of a superconducting material, wherein the assembly further comprises a cooling unit connected to the magnet, the cooling unit configured for maintaining a cryogenic temperature condition within the magnet to enable superconductivity for each of the at least one flux generating element.

13. The assembly as claimed in claim 10, wherein the first position is a retracted position of the magnet into a floor member and the second position is a raised position of the magnet above the floor member for imaging the body portion of the subject.

14. The assembly as claimed in claim 10, further comprising a transmit coil mounted onto an exposed circumferential surface of the gradient coil and extending along a length of the gradient coil, the transmit coil configured to transmit Radio Frequency (RF) pulse rotating net magnetization away from its alignment with main magnetic field.

15. The assembly as claimed in claim 14, wherein the transmit coil is of non-circular shape.

16. The assembly as claimed in claim 10, further comprising a magnet shielding element mounted around a circumferential side surface of a bottom portion of the magnet, the magnet shielding element configured to attenuate a fringe field generated by the at least one flux generating element.

17. An equine Magnetic Imaging Resonance (MRI) system, comprising:

a vertically retractable magnet assembly capable of moving from an upward raised position for imaging to a downward retracted position to allow a subject to move safely, the assembly comprising:

a magnet configured with a bore for receiving the body portion, the bore defining an inner surface of the magnet and extending along a longitudinal axis of the magnet, the magnet comprising at least one flux generating element disposed within the magnet and oriented such that each of the at least one flux generating element surrounds the bore, wherein, each of the at least one flux generating element is configured to generate a magnetic field for magnetizing the body portion positioned within the bore to generate a visual representation of an anatomy of the body portion, and a gradient coil mounted to the inner surface and extending along a length of the bore, the gradient coil is configured for spatial encoding of the magnetic field and is vertically retractable along with the magnet, a positioning system coupled to the magnet and configured to adjust position of the magnet in at least a coordinate axis between a first position and a second position;

a computing device communicably connected to the retractable magnet field assembly, the computing device configured to process a magnetic field interaction of the body portion positioned in the bore of the magnet for generating a visual representation of an anatomy of the body portion; and at least one sensor unit communicably coupled to the positioning system, the at least one sensor unit configured to monitor position of the body portion of the subject, wherein the positioning system is configured to operate between the first position and the second position based on the readings monitored by each of the at least one sensor unit.

18. The system as claimed in claim 17, wherein each of the at least one flux generating element is made of a superconducting material, each of the at least one flux generating element is maintained at a cryogenic temperature condition via a cooling unit coupled to the magnet to enable super-conductivity.

19. The system as claimed in claim 17, wherein the bore of the magnet and the gradient coil are non-circular in shape and are oriented perpendicularly to the longitudinal axis of the magnet.

20. The system as claimed in claim 17, further comprising a transmit coil mounted onto an exposed circumferential surface of the gradient coil and extending along a length of the gradient coil, the transmit coil configured to transmit Radio Frequency (RF) pulse rotating net magnetization away from its alignment with main magnetic field.

21. The system as claimed in claim 20, wherein the transmit coil is of non-circular shape.

22. The system as claimed in claim 17, further comprising a magnet shielding element mounted around a circumferential side surface of a bottom portion of the magnet, the magnet shielding element configured to attenuate a fringe field generated by the at least one flux generating element.

* * * * *